(12) United States Patent
Seward et al.

(10) Patent No.: US 8,708,995 B2
(45) Date of Patent: Apr. 29, 2014

(54) METHODS AND KITS FOR VOLUMETRIC DISTRIBUTION OF PHARMACEUTICAL AGENTS VIA THE VASCULAR ADVENTITIA AND MICROCIRCULATION

(75) Inventors: Kirk Patrick Seward, Dublin, CA (US); Lynn Mateel Barr, Lafayette, CA (US); Judith Carol Wilber, Oakland, CA (US); Robert Cafferata, Santa Rosa, CA (US)

(73) Assignee: Mercator MedSystems, Inc., San Leandro, CA (US)

( * ) Notice: Subject to any disclaimer, the term of this patent is extended or adjusted under 35 U.S.C. 154(b) by 368 days.

(21) Appl. No.: 12/790,541

(22) Filed: May 28, 2010

(65) Prior Publication Data

US 2010/0305546 A1 Dec. 2, 2010

Related U.S. Application Data

(63) Continuation of application No. 10/691,119, filed on Oct. 21, 2003, now Pat. No. 7,744,584, which is a continuation-in-part of application No. 10/350,314, filed on Jan. 22, 2003, now abandoned.

(60) Provisional application No. 60/430,993, filed on Dec. 3, 2002, provisional application No. 60/370,602, filed on Apr. 5, 2002, provisional application No. 60/356,670, filed on Feb. 13, 2002, provisional application No. 60/350,564, filed on Jan. 22, 2002.

(51) Int. Cl.
*A61M 31/00* (2006.01)
*A61M 5/00* (2006.01)

(52) U.S. Cl.
USPC ............... 604/508; 604/116; 604/503

(58) Field of Classification Search
USPC ............... 604/506–8, 510, 511, 93.01, 95.01, 604/116, 117, 103.02, 164.01, 528, 529, 604/532; 600/424, 431, 433–5
See application file for complete search history.

(56) References Cited

U.S. PATENT DOCUMENTS

| | | | |
|---|---|---|---|
| 5,112,305 A | 5/1992 | Barath et al. | |
| 5,196,024 A | 3/1993 | Barath | |
| 5,270,047 A | 12/1993 | Kauffman et al. | |
| 5,354,279 A | 10/1994 | Hofling | |

(Continued)

FOREIGN PATENT DOCUMENTS

WO  WO 01/21157 A2  3/2001

OTHER PUBLICATIONS

Altman et al., Exploring heart lymphatics in local drug delivery, Lymph. Res. Biol., (2003) 1:47-54.

(Continued)

*Primary Examiner* — Manuel Mendez
(74) *Attorney, Agent, or Firm* — Wilson Sonsini Goodrich & Rosati

(57) ABSTRACT

Methods and kits for delivering pharmaceutical agents to the adventitia and other regions outside the external elastic lamina (EEL) surrounding a blood vessel utilize a catheter having a needle. The needle is positioned in up to 5 mm beyond the EEL and delivers an amount of pharmaceutical agent sufficient to circumferentially permeate around the blood vessel and, in many cases, extend longitudinally and radially along the blood vessel. Confirmation that a delivery aperture of the needle lies beyond the EEL may be required before delivering the pharmaceutical agent.

22 Claims, 11 Drawing Sheets

(56) References Cited

U.S. PATENT DOCUMENTS

| | | | |
|---|---|---|---|
| 5,527,532 | A | 6/1996 | Edelman et al. |
| 5,538,504 | A | 7/1996 | Linden et al. |
| 5,645,564 | A | 7/1997 | Northrup et al. |
| 5,681,281 | A | 10/1997 | Vigil et al. |
| 5,693,029 | A | 12/1997 | Leonhardt |
| 5,722,989 | A | 3/1998 | Fitch et al. |
| 5,866,561 | A | 2/1999 | Ungs |
| 6,009,877 | A | 1/2000 | Edwards |
| 6,059,815 | A | 5/2000 | Lee et al. |
| 6,102,933 | A | 8/2000 | Lee et al. |
| 6,210,392 | B1 | 4/2001 | Vigil et al. |
| 6,283,947 | B1 | 9/2001 | Mirzaee |
| 6,302,870 | B1 | 10/2001 | Jacobsen et al. |
| 6,334,856 | B1 | 1/2002 | Allen et al. |
| 6,494,862 | B1 | 12/2002 | Ray et al. |
| 6,547,803 | B2 | 4/2003 | Seward et al. |
| 6,625,486 | B2 | 9/2003 | Lundkvist et al. |
| 6,860,867 | B2 | 3/2005 | Seward et al. |
| 7,094,765 | B1 | 8/2006 | Iversen et al. |
| 7,744,584 | B2 | 6/2010 | Seward et al. |
| 2002/0001581 | A1 | 1/2002 | Lynch et al. |
| 2002/0052404 | A1 | 5/2002 | Hunter et al. |
| 2002/0188310 | A1 | 12/2002 | Seward et al. |
| 2003/0040712 | A1 | 2/2003 | Ray et al. |
| 2003/0078562 | A1 | 4/2003 | Makower et al. |
| 2003/0120297 | A1* | 6/2003 | Beyerlein .............. 606/185 |
| 2003/0171734 | A1 | 9/2003 | Seward et al. |
| 2004/0067197 | A1 | 4/2004 | Leclerc et al. |
| 2004/0162542 | A1 | 8/2004 | Wilber et al. |
| 2004/0260240 | A1* | 12/2004 | Beyerlein .............. 604/117 |
| 2005/0090714 | A1 | 4/2005 | Greff |
| 2005/0158361 | A1 | 7/2005 | Dhondt et al. |
| 2005/0182071 | A1 | 8/2005 | Seward et al. |
| 2005/0232965 | A1 | 10/2005 | Falotico |
| 2006/0069349 | A1* | 3/2006 | Ganz et al. .............. 604/116 |
| 2006/0122684 | A1 | 6/2006 | Lye et al. |
| 2006/0189941 | A1 | 8/2006 | Seward et al. |
| 2007/0078620 | A1 | 4/2007 | Seward et al. |
| 2007/0100318 | A1 | 5/2007 | Seward et al. |
| 2007/0100319 | A1 | 5/2007 | Seward et al. |
| 2007/0100320 | A1 | 5/2007 | Seward et al. |
| 2007/0106248 | A1 | 5/2007 | Seward et al. |
| 2007/0106249 | A1 | 5/2007 | Seward et al. |
| 2007/0106250 | A1 | 5/2007 | Seward et al. |
| 2007/0106251 | A1 | 5/2007 | Seward et al. |
| 2007/0106252 | A1 | 5/2007 | Seward et al. |
| 2007/0106253 | A1 | 5/2007 | Seward et al. |
| 2007/0106254 | A1 | 5/2007 | Seward et al. |
| 2007/0106255 | A1 | 5/2007 | Seward et al. |
| 2007/0106256 | A1 | 5/2007 | Seward et al. |
| 2007/0106257 | A1 | 5/2007 | Seward et al. |

OTHER PUBLICATIONS

Ayers et al., "Amiodarone instilled into the canine pericardial sac migrates transmurally to produce electrophysiologic effects and suppress atrial fibrillation,".

Barath et al., "Infiltrator Angioplasty Balloon Catheter: a device for combined angioplasty and intramural site-specific treatment," Cathet Cardiovasc Diagn. Jul. 1997;41(3):333-341.

Chandrasekar et al., "Coronary Artery Endothelial Protection After Local Delivery of 17β-Estradiol During Balloon Angioplasty in a Porcine Model : A Potential New Pharmacologic Approach to Improve Endothelial Function," J. Am. Col. Cardiol. (2001), 38(5):1570-1576.

Chandrasekar et al., "Local Delivery of 17-Beta-Estradiol Decreases Neointimal Hyperplasia After Coronary Angioplasty in a Porcine Model," J. Am. Col. Cardiol. (2000), 36(6):1972-1978.

Creel, "Arterial Paclitaxel Distribution and Deposition," Circulation Research. Apr. 2000;86:879-884.

Dai-Do et al., "17 beta-estradiol inhibits proliferation and migration of human vascular smooth muscle cells: similar effects in cells from postmenopausal females and in males," Cardiovasc Res. Nov. 1996;32(5):980-985.

Daschner et al., Penetration of gentamicin into heart valves, subcutaneous and muscular tissue of patients undergoing open heart surgery, J. Cardiovasc. Surg., (1986) 581-584.

Laham et al., Intracoronary and intravenous administration of basic fibroblast growth factor: myocardial and tissue distribution, Drug Met. Disp., (1999) 27:821-826.

Laham et al., Intrapericardial administration of basic fibroblast growth factor: myocardial and tissue distribution and comparison with intracoronary and intravenous administration, Cath Cardio. Interv., (2003) 58:375-381.

Nikol et al., "Needle Injection Catheter Delivery of the Gene for an Antibacterial Agent Inhibits Neointimal Formation," Gene Therapy, May 1999, vol. 6, No. 5, pp. 737-748.

Pharmacia & Upjohn Company, "Depo-Estradiol," Product/Prescription Information [pamphlet], (Aug. 2000), 6 pages total.

Solmon et al., "Amiodarone versus a β-blocker to prevent atrial fibrillation after cardiovascular surgery," AHJ, Nov. 2001; 142(5):811-815.

U.S. Appl. No. 60/356,670, filed Feb. 13, 2002; first named inventor: Kirk Patrick Seward.

International search report dated Apr. 21, 2004 for PCT/US2003/002130.

* cited by examiner

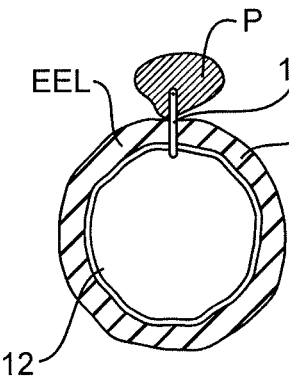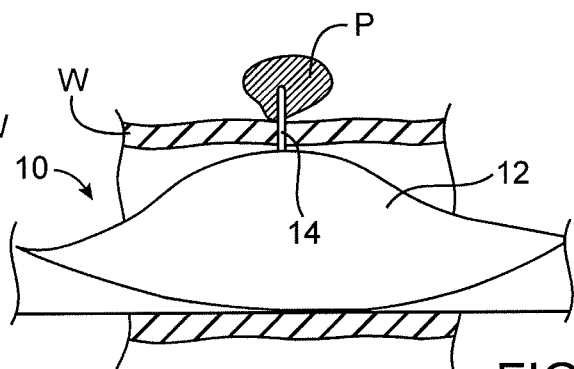
FIG. 6A  FIG. 6B
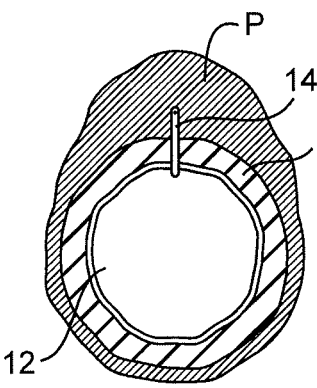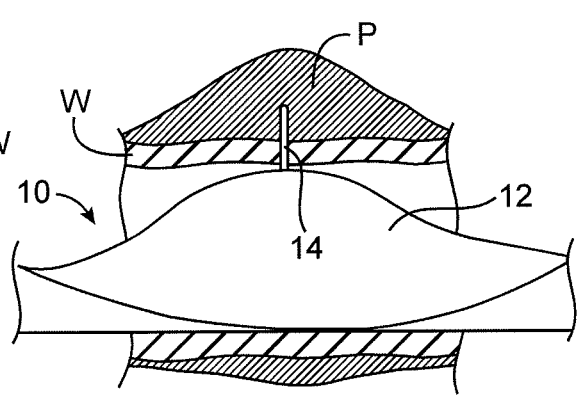
FIG. 7A  FIG. 7B
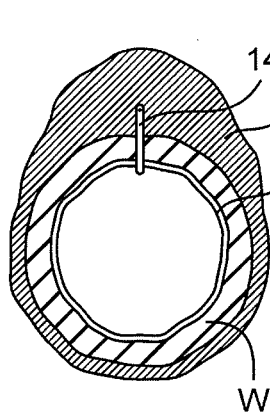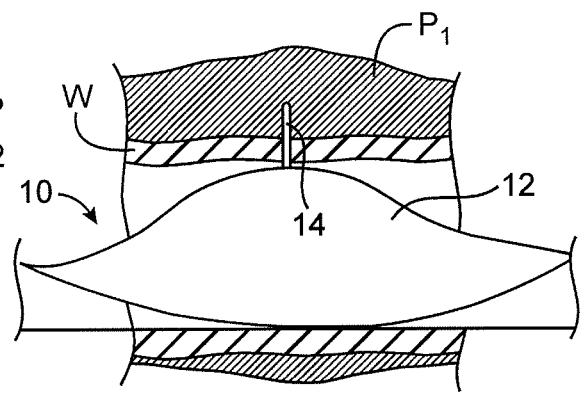
FIG. 8A  FIG. 8B

METHODS AND KITS FOR VOLUMETRIC DISTRIBUTION OF PHARMACEUTICAL AGENTS VIA THE VASCULAR ADVENTITIA AND MICROCIRCULATION

CROSS-REFERENCES TO RELATED APPLICATIONS

This application is a continuation of Ser. No. 10/691,119, filed on Oct. 21, 2003, which is a continuation-in-part of application Ser. No. 10/350,314, filed on Jan. 22, 2003, which claimed the benefit of each of the following provisional applications, 60/350,564, filed Jan. 22, 2002; 60/356,670, filed Apr. 5, 2002; 60/370,602, filed Apr. 5, 2002; and 60/430,993, filed Dec. 3, 2002. The full disclosures of each of these prior provisional and non-provisional applications are incorporated herein by reference.

BACKGROUND OF THE INVENTION

1. Field of the Invention

The present invention relates generally to medical methods and devices. More particularly, the present invention relates to medical methods and kits for distributing pharmaceutical agents in the adventitial tissue surrounding a blood vessel.

Coronary artery disease is the leading cause of death and morbidity in the United States and other western societies. In particular, atherosclerosis in the coronary arteries can cause myocardial infarction, commonly referred to as a heart attack, which can be immediately fatal or, even if survived, can cause damage to the heart which can incapacitate the patient. Other coronary diseases which cause death and incapacitation include congestive heart failure, vulnerable or unstable plaque, and cardiac arrhythmias. In addition to coronary artery disease, diseases of the peripheral vasculature can also be fatal or incapacitating. Blood clots and thrombus may occlude peripheral blood flow, leading to tissue and organ necrosis. Deep vein thrombosis in the legs can, in the worse cases, requiring amputation. Clots in the carotid artery can embolize and travel to the brain, potentially causing ischemic stroke.

While coronary artery bypass surgery is an effective treatment for stenosed arteries resulting from atherosclerosis and other causes, it is a highly invasive procedure which is also expensive and which requires substantial hospital and recovery time. Percutaneous transluminal coronary angioplasty (PTCA), commonly referred to as balloon angioplasty, is less invasive, less traumatic, and significantly less expensive than bypass surgery. Until recently, however, balloon angioplasty has not been considered to be as effective a treatment as bypass surgery. The effectiveness of balloon angioplasty, however, has improved significantly with the introduction of stenting which involves the placement of a scaffold structure within the artery which has been treated by balloon angioplasty. The stent inhibits abrupt reclosure of the artery and has some benefit in reducing subsequent restenosis resulting from hyperplasia.

Despite such improvement, patients who have undergone angioplasty procedures with subsequent stenting still suffer from a high incidence of restenosis resulting from hyperplasia. Very recently, however, experimental trials have demonstrated that the implanting of stents which have been coated with anti-proliferative drugs can significantly reduce the occurrence of hyperplasia, promising to make combined angioplasty and stenting a viable alternative to bypass surgery.

As an alternative to stent-based luminal drug delivery, the direct delivery of drug into vascular and other luminal walls has been proposed. For some time, the use of intravascular catheters having porous balloons, spaced-apart isolation balloons, expandable sleeves, and the like, have been used for releasing drugs into the inner surface of the endothelial wall of blood vessels.

Congestive heart failure and cardiac arrhythmias, although sometimes related to coronary artery disease, are usually treated differently than are occlusive diseases. Congestive heart failure is most often treated pharmaceutically, although no particular drug regimens have proven to be highly effective. Proposed mechanical approaches for treating congestive heart failure include constraints for inhibiting further dilation of the heart muscle, and pace makers and mechanical devices for enhancing heart function. Cardiac arrhythmias may also be treated with drug therapies, and reasonably effective intravascular treatments for ablating aberrant conductive paths on the endocardial surfaces also exist. No one treatment, however, for either of these conditions is completely effective in all cases.

Of particular interest to the present invention, catheters carrying microneedles capable of delivering therapeutic and other agents deep into the adventitial layer surrounding blood vessel lumens have been described in U.S. Pat. No. 6,547,303, and co-pending application Ser. No. 09/961,079, filed on Sep. 20, 2001, both having common inventorship with but different assignment than the present application, the full disclosures of which are incorporated herein by reference.

Pharmaceutical therapies for coronary artery and other cardiac and vascular diseases can be problematic in a number of respects. First, it can be difficult to achieve therapeutically effective levels of a pharmaceutical agent in the cardiac tissues of interest. This is particularly true of systemic drug delivery, but also true of various intravascular drug delivery protocols which have been suggested. The release of a pharmaceutical agent directly on to the surface of a blood vessel wall within the heart or the peripheral vasculature frequently results in much or most of the drug being lost into the luminal blood flow. Thus, drugs which are difficult to deliver across the blood vessel wall will often not be able to reach therapeutically effective concentrations in the targeted tissue. Second, even when drugs are successfully delivered into the blood vessel wall, they will frequently lack persistence, i.e., the drug will be rapidly released back into the blood flow and lost from the targeted tissues. Third, it is frequently difficult to intravascularly deliver a pharmaceutical agent to remote and/or distributed diseased regions within a blood vessel. Most prior intravascular drug delivery systems, at best, deliver relatively low concentrations of the pharmaceutical agent into regions of the blood vessel wall which are directly in contact with the delivery catheter. Thus, diseased regions which may be remote from the delivery site(s) and/or which include multiple spaced-apart loci may receive little or no therapeutic benefit from the agent being delivered. In particular, most if not all prior intravascular drug delivery apparatus have been unable to deliver the drug over large volumetric regions of tissue, particularly in a manner which achieves relatively consistent drug concentrations. Fourth, delivery of a pharmaceutical agent into the blood vessel wall may be insufficient to treat the underlying cause of disease. For example, delivery of anti-proliferative agents into the blood vessel wall may have limited benefit in inhibiting the smooth muscle cell migration which is believed to be a cause of intimal hyperplasia or cell proliferation characteristic of neoplastic diseases. Fifth, the etiology of the vascular disease may itself inhibit effective delivery of a pharmaceutical agent. Thus, systems and protocols which are designed to deliver drug into blood vessel wall at the site of disease may be limited in their effectiveness by the nature of the disease itself.

For these reasons, it would be desirable to provide additional and improved methods and kits for the intravascular delivery of pharmaceutical agents to treat coronary cerebral, hepatic, peripheral, and other vascular diseases. Such additional and improved methods and kits would preferably also be adaptable to treat non-vascular diseases, including cancers and other neoplastic diseases, diseases associated with particular organs or other compartmentalized tissue regions, and other conditions which might benefit from remote localized delivery of drugs via the vasculature. In particular, it would be beneficial to provide methods which enhance the therapeutic concentrations of the pharmaceutical agents in diseased and other targeted tissues, not just the blood vessel walls. For example, it would be particularly desirable if the methods and systems could provide for an extended volumetric distribution of the delivered pharmaceutical agent including both longitudinal and radial spreading from the injection site(s) in order to provide therapeutic dosage levels of the agent within the heart, liver, or other organ or compartmentalized tissue region. It would be further beneficial if the methods could efficiently deliver the drugs into the targeted tissue and limit or avoid the loss of drugs into the luminal blood flow. Similarly, it would be beneficial to enhance the therapeutic concentrations of the pharmaceutical agent delivered to a particular targeted tissue. It would be still further beneficial if the persistence of such therapeutic concentrations of the pharmaceutical agent in the tissue were also increased, particularly in targeted tissues away from the blood vessel wall, including the adventitial tissue surrounding the blood vessel wall. Additionally, it would be beneficial to increase the uniformity and extent of pharmaceutical agent delivery over remote, extended, and distributed regions of the adventitia and other tissues surrounding the blood vessels. In some instances, it would be beneficial to provide methods which permit the delivery of pharmaceutical agents through the blood vessel walls at non-diseased sites within the blood vessel, where the agent would then be able to migrate through the adventitia or other tissues to the diseased site(s). At least some of these objectives will be met by the inventions described hereinafter. Still further, it would be desirable if such intravascular delivery of pharmaceutical agents would be useful for treating diseases and conditions of the tissues and organs in addition to those directly related to the heart or vasculature.

2. Description of the Background Art

U.S. Pat. No. 6,547,803 B2, and published Application 2003/0171734A1 both having common inventorship with but different assignment than the present application, describe microneedle catheters which may be used in at least some of the methods described in the present application. Drug distribution through the collateral circulation in the heart is discussed in Daschner et al. (1986) J. Cardiovasc. Surg. 581-584; Laham et al. (1999) Drug Met. Disp. 27:821-826; Laham et al. (2003) Cath. Cardio. Interv. 58:375-381; and Altman et al. (2003) Lymph. Res. Biol. 1:47-54.

BRIEF SUMMARY OF THE INVENTION

Methods and kits according to the present invention are able to achieve enhanced concentrations of many pharmaceutical agents in targeted tissues surrounding a blood vessel, particularly adventitial tissues, more particularly coronary adventitial tissues. The methods rely on intravascular delivery of the pharmaceutical agent using a catheter having a deployable needle, usually a small needle or a microneedle. The catheter is advanced intravascularly to a target injection site (which may or may not be a diseased region) in a blood vessel. The needle is advanced through the blood vessel wall so that an aperture on the needle is positioned in a perivascular region (defined below) surrounding the injection site, and the pharmaceutical agent is delivered into the perivascular region through the microneedle.

In particular, the methods of the present invention are intended for a volumetric distribution of a pharmaceutical agent in the tissue of a living host. By "volumetric distribution," it is meant that the pharmaceutical agent will be able to distribute both longitudinally and radially with respect to the axis of the blood vessel from which the agent is being injected. Typically, the agent will be able to distribute over a distance of at least 1 cm longitudinally and at least 1 cm radially from the site of injection over a time period no greater than 60 minutes. Usually, the volumetric distribution will be significantly greater than that, and a concentration of the agent measured at all locations at least 2 cm from the delivery site will be at least 10% of the concentration at the delivery site, again preferably after a period of 60 minutes.

While the present invention does not depend upon an understanding of the distribution mechanism, for completeness, it is noted that the inventors herein believe that this volumetric distribution results from delivery of the pharmaceutical agent into the lymphatic micro circulatory system surrounding the blood vessel from which the agent is directed.

Regardless of the actual mechanism, the methods herein preferably rely on positioning an aperture of the needle within the target blood vessel so that the aperture lies beyond an external elastic lamina (EEL) of the blood vessel wall by a distance not exceeding 5 mm, usually not exceeding 3 mm, and preferably not exceeding 0.5 mm. The lower end of the range is less critical, and it is necessary only that the aperture be at least partly beyond the other periphery of the EEL. For lymphatic distribution, it is preferred to deliver pharmaceutical agents having dimensions which do not exceed 200 nm, as larger substances are not efficiently distributed by the lymphatic distribution system.

The methods, systems, and kits of the present invention will find particular use in the coronary vasculature, including the arterial and venous vasculature, for treating a variety of conditions, including post-angioplasty and post-stenting hyperplasia, cardiac failure, coronary revascularization, and the like. The present invention will, however, also find use outside of the coronary vasculature, including but not limited to use in the cerebral vasculature, the hepatic vasculature, the peripheral vasculature, and the vasculature of other organs and tissue compartments within a patient. The pharmaceutical agents may be delivered to treat virtually any condition which is amenable to localized drug delivery, including the delivery of anti-neoplastic agents to treat tumors and other neoplastic conditions, the delivery of antibiotics and other anti-infective agents to treat infections and other pathogen-based diseases, and the like.

This delivery protocol has been found to have a number of unexpected advantages. First, direct injection into the perivascular region has been found to immediately provide relatively high concentrations of the pharmaceutical agent in volume immediately surrounding the injected tissue. Second, following injection, it has been found that the injected agents will distribute circumferentially to substantially uniformly surround the blood vessel at the injection site as well as longitudinally to reach positions which are 1 cm, 2 cm, 5 cm, or more away from the injection site. In particular, the injected pharmaceutical agents have been found to distribute transmurally throughout the endothelial and intimal layers of the blood vessel, as well as in the media, or muscular layer, of the blood vessel wall. In the coronary arteries, in addition to circumferential and longitudinal migration, the pharmaceutical agent can migrate through the myocardium to reach the adventitia and wall structures surrounding blood vessels other than that through which the agent has been injected. Pathways for the distribution of the pharmaceutical agent are presently believed to exist through the pericardial space and the sub-epicardial space and may also exist in the vasa vasorum and other capillary channels through the muscle and connective tissues. Third, the delivered and distributed pharmaceutical agent(s) will persist for hours or days and will release back into the blood vessel wall over time. Thus, a prolonged therapeutic effect based on the pharmaceutical agent may be achieved in both the adventitia and the blood vessel wall. Fourth, after the distribution has occurred, the concentration of the pharmaceutical agent throughout its distribution region will be highly uniform. While the concentration of the pharmaceutical agent at the injection site will always remain the highest, concentrations at other locations in the peripheral adventitia around the injection site will usually reach at least about 10% of the concentration at the injection site, often being at least about 25%, and sometimes being at least about 50%. Similarly, concentrations in the adventitia at locations longitudinally separated from the injection site by about 5 cm will usually reach at least 5% of the concentration at the injection site, often being at least 10%, and sometimes being at least 25%. Finally, the methods of the present invention will allow for the injection of pharmaceutical agents through non-diseased regions of the coronary and peripheral vasculature to treat adjacent or remote diseased regions of the vasculature. The latter is of particular advantage since the diseased regions may be refractory to effective microneedle or other intravascular delivery protocols. Thus, pharmaceutical agent(s) can be delivered into the adventitia surrounding the diseased regions through remote injection sites.

The benefits of the present invention are achieved by delivering the pharmaceutical agents into a perivascular region surrounding a coronary artery or other blood vessel. The perivascular region is defined as the region beyond external elastic lamina of an artery or beyond the tunica media of a vein. Usually, injection will be made directly into the vasa vasorum region of the adventitia, and it has been found that the pharmaceutical agent disperses through the adventitia circumferentially, longitudinally, and transmurally from injection site. Such distribution can provide for delivery of therapeutically effective concentrations of many drugs which would be difficult to administer in other ways.

The adventitia is a layer of fatty tissue surrounding the arteries of the human and other vertebrate cardiovascular systems. The external elastic lamina (EEL) separates the fatty adventitial tissue from muscular tissue that forms the arterial wall. Microneedles of the present invention pass through the muscular tissue of the blood vessel and the EEL in order to reach the perivascular space into which the drug is injected. The drugs will typically either be in fluid form themselves, or will be suspended in aqueous or fluid carriers in order to permit dispersion of the pharmaceutical agents through the adventitia.

The adventitial tissue has a high concentration of lipids which will preferentially solubilize lipophilic pharmaceutical agents and hydrophilic or other pharmaceutical agents which are incorporated into lipophilic carriers, adjuvants, or the like. Both lipophilic and non-lipophilic pharmaceutical agents will have the ability to diffuse within and through the adventitia, with the rate and extent of such diffusion being controlled, at least in part, by the degree and nature of the lipophilic moieties present in the pharmaceutical agents. Thus, when pharmaceutical agents are injected, either by themselves or in an aqueous carrier, the agents may tend to be preferentially absorbed by the lipids in the adventitia. Pharmaceutical agents do not, however, remain localized at the site of injection, but instead will migrate and spread through the adventitia to locations remote from the injection site. The affinity between the pharmaceutical agents and the lipids in the adventitia, however, will provide for a controlled and sustained release of the lipophilic and other pharmaceutical agents over time. Thus, delivery of pharmaceutical agents into the adventitia creates a biological controlled release system for the agents. In particular, the pharmaceutical agents will slowly be released back from the adventitia into the muscle and other layers of the blood vessel wall to provide for prolonged pharmacological treatment of those areas. Such prolonged treatments can be particularly useful for inhibiting vascular hyperplasia and other conditions which are thought to initiate within the smooth muscle cells and other components of the blood vessel wall.

Pharmaceutical agents formulated to provide for sustained or controlled release of the pharmacologically active substances may be introduced directly into the adventitia by injection using the microneedle of the present invention. Numerous particular controlled release formulations are known in the art. Exemplary formulations include those which provide for diffusion through pores of a microcarrier or other particle, erosion of particles or barrier films, and combinations thereof. In addition, microparticles or nanoparticles of pure (neat) pharmaceutical substances may be provided. Cross-linked forms of such substances may also be utilized, and combinations thereof with erodable polymers may be employed. Other conventional formulations, such as liposomes, solubilizers (e.g. cyclodextrins), and the like, may be provided to control release of the active substance in the pharmaceutical agent.

In a first aspect of the present invention, a method for distributing a pharmaceutical agent in the adventitial tissue of a living vertebrate host's heart, such as a human heart, comprises positioning a microneedle through the wall of a coronary blood vessel and delivering an amount of the pharmaceutical agent therethrough. The aperture of the microneedle is located in a perivascular space surrounding the blood vessel, and the pharmaceutical agent distributes substantially completely circumferentially through adventitial tissue surrounding the blood vessel at the site of the microneedle. Usually, the agent will further distribute longitudinally along the blood vessel over a distance of at least 1 cm, often a distance of a least 5 cm, and sometimes a distance of at least 10 cm, within a time period no greater than 60 minutes, often within 5 minutes of less. While the concentration of the pharmaceutical agent in the adventitia will decrease in the longitudinal direction somewhat, usually, the concentration measured at a distance of 5 cm from the injection site will be at least 5% of the concentration measured at the same time at the injection site, often being at least 10%, frequently being as much as 25%, and sometimes being as much as 50%.

The aperture of the microneedle will be positioned so that it lies beyond the external elastic lamina (EEL) of the blood vessel wall and into the perivascular region surrounding the wall. Usually, the aperture will be positioned at a distance from the inner wall of the blood vessel which is equal to at least 10% of the mean luminal diameter of the blood vessel at the injection site. Preferably, the distance will be in the range from 10% to 75% of the mean luminal diameter. The amounts of the pharmaceutical agent delivered into the perivascular region may vary considerably, but will typically be in the range from 10 µl to 5000 µl, typically being from 100 µl to 1000 µl, and often being from 250 µl to 500 µl. Such methods for distributing pharmaceutical agents will be most often used in coronary arteries, typically for the treatment of hyperplasia or vulnerable plaque. The methods may further find use, however, in patients suffering from other vascular diseases, such as those in the peripheral vasculature, and in patients suffering from coronary conditions, including congestive heart failure, cardiac arrhythmias, and the like. In the latter cases, the methods of the present invention are particularly useful in delivering pharmaceutical agents widely and uniformly through the myocardium by using one or a relatively low number of injections in the coronary vasculature.

In a second aspect of the present invention, methods for depoting a lipophilic or other pharmaceutical agent in the adventitial tissue of a living vertebrate host, typically a human heart or other tissue, comprise positioning a microneedle through the wall of a coronary blood vessel and delivering an amount of the pharmaceutical agent into the perivascular space surrounding the blood vessel. The agent is delivered through an aperture in the microneedle directly into the perivascular space so that it distributes within the adventitial tissue surrounding the blood vessel. As described generally above, the interaction between the pharmaceutical agent and the lipid-containing adventitia provide for a depot or reservoir of the drug which is subsequently released into the blood vessel wall and other tissues in a controlled fashion over time. While the depoting pharmaceutical agent in the coronary adventitial tissue may find the greatest use, the depoting and release of drugs from other adventitial tissues located surrounding the peripheral vasculature will also find use in the treatment of peripheral vascular disease, as well as diseases of other organs and tissues.

Exemplary pharmaceutical agents for treating restenosis and hyperplasia include antiproliferative agents, immunosuppressive agents, anti-inflammatory agents, macrolide antibiotics, statins, anti-sense agents, metalloproteinase inhibitors, and cell cycle inhibitors and modulators. Agents for the treatment of arrhythmia include amiodarone, ibutilide, and mexiletine. Agents for the treatment of congestive heart failure include beta blockers, nitric oxide releasers, angiotensin converting enzyme inhibitors, and calcium channel antagonists. Agents for treatment of vulnerable (unstable) plaque include macrolide antibiotics, anti-inflammatory agents, statins, and thioglitazones. Agents for the treatment of vasospasm include cerapamil, and lapararin. A more complete listing of pharmaceutical agents suitable for treating coronary, vascular, and other diseased tissues and organs in accordance with the principles of the present invention is set forth in Table I below.

In a third aspect of the present invention, a method for delivering a pharmaceutical agent to a diseased treatment region in a coronary blood vessel comprises positioning a microneedle through the wall of a coronary artery at a delivery site spaced-apart from the diseased treatment region. The delivery site may be located within the same blood vessel as the diseased treatment region at a location which is longitudinally spaced-apart from said region, or may be located in a different blood vessel, including a different artery, or more usually, in a cognate coronary vein. In all cases, an amount of the pharmaceutical agent is delivered through an aperture in the microneedle into a perivascular space surrounding the delivery site so that the agent distributes into adventitial tissue surrounding the diseased treatment region to provide for the desired therapy. In some instances, the diseased treatment region may have been previously stented where the delivery site is spaced away from the stent, either longitudinally away from the stent in the same coronary artery or remote from the stent in another coronary artery or vein.

In still further aspects of the present invention, kits for delivering pharmaceutical agents to a patient suffering from or at risk of coronary artery or other vascular or non-vascular disease comprise a catheter and instructions for use of the catheter. The catheter has a microneedle which can be advanced from a blood vessel lumen through a wall of the blood vessel to position an aperture of the microneedle at a perivascular space surrounding the blood vessel. The instructions for use set forth any of the three exemplary treatment protocols described above.

The present invention still further comprises the use of a catheter having a microneedle in the manufacture of an apparatus for delivering pharmaceutical agents to a patient suffering from coronary artery disease. The pharmaceutical agent is delivered from a blood vessel lumen into a perivascular space surrounding the blood vessel so that the agent distributes circumferentially through the adventitial tissue surrounding the blood vessel. Usually, the agent will also distribute longitudinally along the blood vessel over a distance of at least 5 cm within a time of no greater than 5 minutes, usually within 1 minute or less. In some cases, the agent may further distribute into regions of the adventitia surrounding other blood vessels.

In another aspect of the present invention, methods and apparatus are provided for confirming that the aperture of the pharmaceutical agent injection needle is present beyond the external elastic lamina (EEL) before delivering pharmaceutical agent. As discussed above, it will often be desirable to place the delivery aperture of the pharmaceutical agent delivery needle just beyond the outside periphery or perimeter of the EEL prior to injection of the desired pharmaceutical agent. The difficulty with such positioning is that the thickness of the EEL can vary significantly, typically being from 0.1 mm to 5 mm thick, usually being less than 3 mm thick. The effective deployed needle length may not always be sufficient to assure that the delivery aperture is in the preferred 0 mm to 5 mm cylindrical envelope region outside of the EEL. Moreover, variations in thickness of plaque and other obstructive material which may be present on the interior of the blood vessel can also affect the ability of the needle to penetrate the vascular wall and position the delivery aperture at the requisite distance beyond the periphery of the EEL. Thus, in order to assure that the drug will enter this preferred cylindrical envelope surrounding the blood vessel, it is useful to confirm the position of the delivery aperture prior to delivery of the pharmaceutical agent.

Confirmation of the position of the pharmaceutical agent delivery aperture can be achieved in a variety of ways. Most simply, a bolus of radio opaque contrast agent or other visible media can be injected through the needle after initial positioning of the needle is achieved. By then observing the distribution of the media, usually fluoroscopically, the position of the aperture can be assessed. If the needle still lies within the EEL, the bolus will remain contained within the wall and will appear to have well defined edges and will usually taper longitudinally as the wall is dissected. If the aperture is properly positioned outside of the EEL, in contrast, the media will diffuse longitudinally along the vessel in the desired pattern. Finally, if the needle has extended beyond the preferred adventitial space and into muscle, the media will usually follow a non-homogenous diffusion pattern between the muscle fibers. Only when the desired pattern characteristic of adventitial delivery is confirmed will the pharmaceutical agent then be delivered.

In other cases, various sensors can be attached or otherwise coupled to the delivery needle, usually near the delivery aperture, in order to detect the position of the needle. Useful sensors include temperature sensors, pH sensors, electrical impedance sensors, and the like. It is also possible to measure back pressure on an injected fluid, either saline or other non-active agent or the pharmaceutical agent itself, in order to determine the needle position. Injection into the blood vessel wall will typically result in a greater back pressure than injection into the adventitial space. It will also be possible to monitor the insertion force of the needle, e.g., by providing a deflection gauge on a portion of the needle, or otherwise.

BRIEF DESCRIPTION OF THE DRAWINGS

FIGS. 6A and 6B illustrate the initial stage of the injection of a pharmaceutical agent into a perivascular space using the catheter of FIG. 3. FIG. 6A is a view taken across the blood vessel and FIG. 6B is a view taken along the longitudinal length of the blood vessel.

FIGS. 7A and 7B are similar to FIGS. 6A and 6B showing the extent of pharmaceutical agent distribution at a later time after injection.

FIGS. 8A and 8B are again similar to FIGS. 6A and 6B showing the extent of pharmaceutical agent distribution at a still later time following injection.

DETAILED DESCRIPTION OF THE INVENTION

The present invention will preferably utilize microfabricated catheters for intravascular injection. The following description provides two representative embodiments of catheters having microneedles suitable for the delivery of a pharmaceutical agent into a perivascular space or adventitial tissue. A more complete description of the catheters and methods for their fabrication is provided in U.S. Pat. No. 6,547,803 B2 the full disclosure of which has been incorporated herein by reference.

Figure 1:
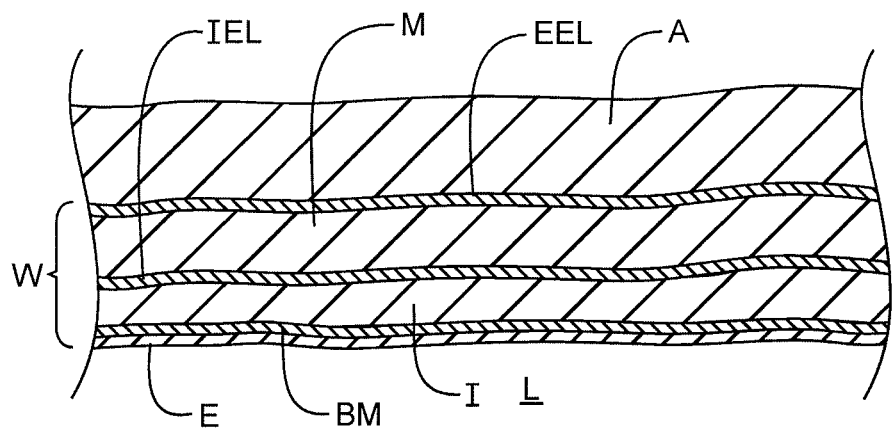
FIG. 1 is a schematic illustration of a coronary artery together with surrounding tissue illustrating the relationship between the perivascular space, the adventitia, and the blood vessel wall components.
Figure 1A:
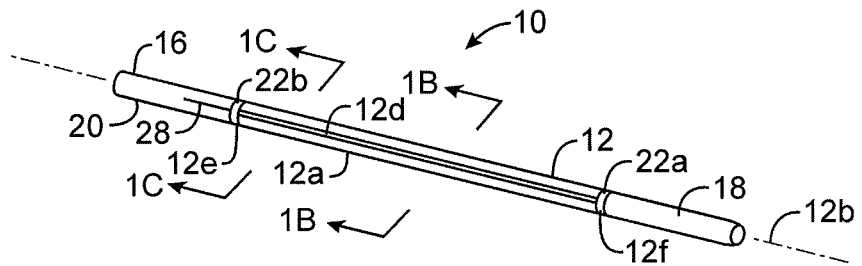
FIG. 1A is a schematic, perspective view of a microfabricated surgical device for interventional procedures in accordance with the methods and kits of the present invention in an unactuated condition.

The perivascular space is the potential space over the outer surface of a "vascular wall" of either an artery or vein. Referring to FIG. 1, a typical arterial wall is shown in cross-section where the endothelium E is the layer of the wall which is exposed to the blood vessel lumen L. Underlying the endothelium is the basement membrane BM which in turn is surrounded by the intima I. The intima, in turn, is surrounded by the internal elastic lamina IEL over which is located the media M. In turn, the media is covered by the external elastic lamina (EEL) which acts as the outer barrier separating the arterial wall, shown collectively as W, from the adventitial layer A. Usually, the perivascular space will be considered anything lying beyond the external elastic lamina EEL, including regions within the adventitia and beyond.

The microneedle is inserted, preferably in a substantially normal direction, into the wall of a vessel (artery or vein) to eliminate as much trauma to the patient as possible. Until the microneedle is at the site of an injection, it is positioned out of the way so that it does not scrape against arterial or venous walls with its tip. Specifically, the microneedle remains enclosed in the walls of an actuator or sheath attached to a catheter so that it will not injure the patient during intervention or the physician during handling. When the injection site is reached, movement of the actuator along the vessel terminated, and the actuator is operated to cause the microneedle to be thrust outwardly, substantially perpendicular to the central axis of a vessel, for instance, in which the catheter has been inserted.

Figure 1B:
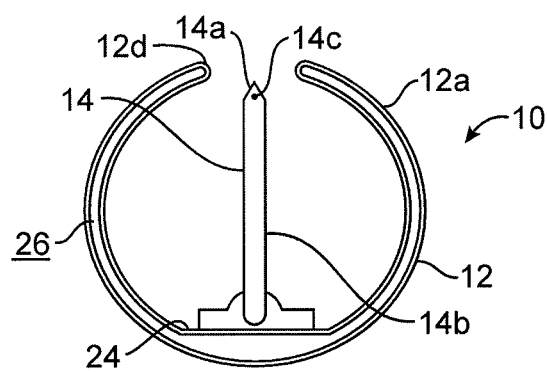
FIG. 1B is a schematic view along line 1B-1B of FIG. 1A.
Figure 1C:
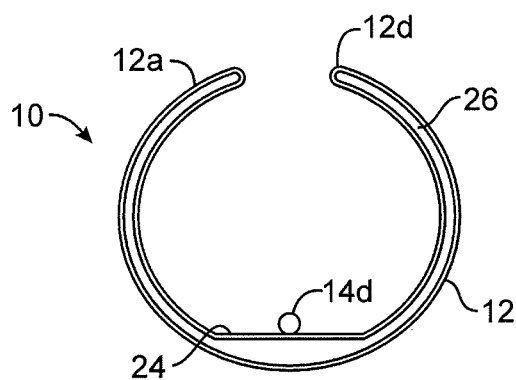
FIG. 1C is a schematic view along line 1C-1C of FIG. 1A.
Figure 2A:
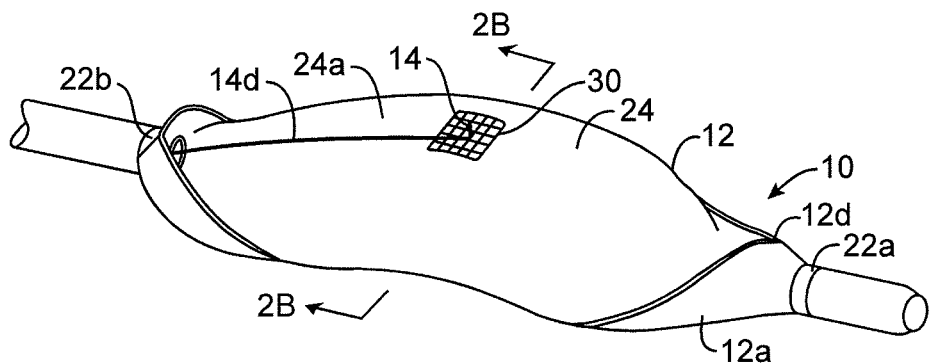
FIG. 2A is a schematic, perspective view of the microfabricated surgical device of FIG. 1A in an actuated condition.
Figure 2B:
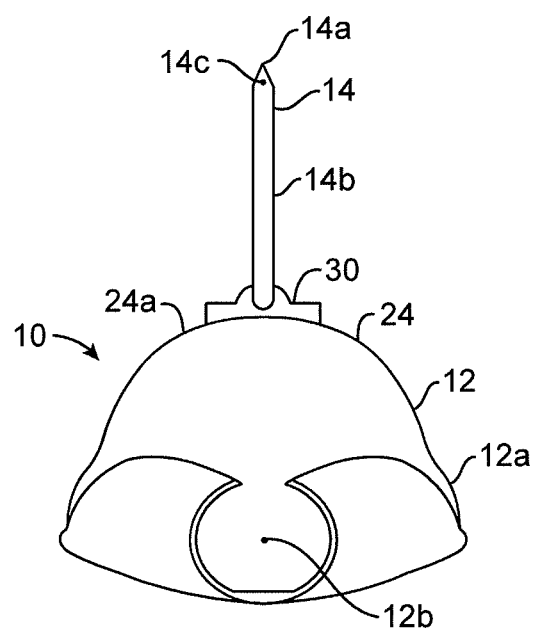
FIG. 2B is a schematic view along line 2B-2B of FIG. 2A.

As shown in FIGS. 1A-2B, a microfabricated intravascular catheter 10 includes an actuator 12 having an actuator body 12a and central longitudinal axis 12 b. The actuator body more or less forms a C-shaped outline having an opening or slit 12d extending substantially along its length. A microneedle 14 is located within the actuator body, as discussed in more detail below, when the actuator is in its unactuated condition (furled state) (FIG. 1B). The microneedle is moved outside the actuator body when the actuator is operated to be in its actuated condition (unfurled state) (FIG. 2B).

The actuator may be capped at its proximal end 12e and distal end 12f by a lead end 16 and a tip end 18, respectively, of a therapeutic catheter 20. The catheter tip end serves as a means of locating the actuator inside a blood vessel by use of a radio opaque coatings or markers. The catheter tip also forms a seal at the distal end 12f of the actuator. The lead end of the catheter provides the necessary interconnects (fluidic, mechanical, electrical or optical) at the proximal end 12e of the actuator.

Retaining rings 22a and 22b are located at the distal and proximal ends, respectively, of the actuator. The catheter tip is joined to the retaining ring 22a, while the catheter lead is joined to retaining ring 22b. The retaining rings are made of a thin, on the order of 10 to 100 microns (μm), substantially rigid material, such as parylene (types C, D or N), or a metal, for example, aluminum, stainless steel, gold, titanium or tungsten. The retaining rings form a rigid substantially "C"-shaped structure at each end of the actuator. The catheter may be joined to the retaining rings by, for example, a butt-weld, an ultra sonic weld, integral polymer encapsulation or an adhesive such as an epoxy.

The actuator body further comprises a central, expandable section 24 located between retaining rings 22a and 22b. The expandable section 24 includes an interior open area 26 for rapid expansion when an activating fluid is supplied to that area. The central section 24 is made of a thin, semi-rigid or rigid, expandable material, such as a polymer, for instance, parylene (types C, D or N), silicone, polyurethane or polyimide. The central section 24, upon actuation, is expandable somewhat like a balloon-device.

The central section is capable of withstanding pressures of up to about 100 atmospheres upon application of the activating fluid to the open area 26. The material from which the central section is made of is rigid or semi-rigid in that the central section returns substantially to its original configuration and orientation (the unactuated condition) when the activating fluid is removed from the open area 26. Thus, in this sense, the central section is very much unlike a balloon which has no inherently stable structure.

The open area 26 of the actuator is connected to a delivery conduit, tube or fluid pathway 28 that extends from the catheter's lead end to the actuator's proximal end. The activating fluid is supplied to the open area via the delivery tube. The delivery tube may be constructed of Teflon© or other inert plastics. The activating fluid may be a saline solution or a radio-opaque dye.

The microneedle 14 may be located approximately in the middle of the central section 24. However, as discussed below, this is not necessary, especially when multiple microneedles are used. The microneedle is affixed to an exterior surface 24a of the central section. The microneedle is affixed to the surface 24a by an adhesive, such as cyanoacrylate. The mesh-like structure (if included) may be-made of, for instance, steel or nylon.

The microneedle includes a sharp tip 14a and a shaft 14b. The microneedle tip can provide an insertion edge or point. The shaft 14b can be hollow and the tip can have an outlet port 14c, permitting the injection of a pharmaceutical or drug into a patient. The microneedle, however, does not need to be hollow, as it may be configured like a neural probe to accomplish other tasks.

As shown, the microneedle extends approximately perpendicularly from surface 24a. Thus, as described, the microneedle will move substantially perpendicularly to an axis of a vessel or artery into which has been inserted, to allow direct puncture or breach of vascular walls.

The microneedle further includes a pharmaceutical or drug supply conduit, tube or fluid pathway 14d which places the microneedle in fluid communication with the appropriate fluid interconnect at the catheter lead end. This supply tube may be formed integrally with the shaft 14b, or it may be formed as a separate piece that is later joined to the shaft by, for example, an adhesive such as an epoxy.

The needle 14 may be a 30-gauge, or smaller, steel needle. Alternatively, the microneedle may be microfabricated from polymers, other metals, metal alloys or semiconductor materials. The needle, for example, may be made of parylene, silicon or glass. Microneedles and methods of fabrication are described in U.S. patent publication 2002/0188310, entitled "Microfabricated Surgical Device", having common inventorship with but different assignment than the subject application, the entire disclosure of which is incorporated herein by reference.

Figure 3:
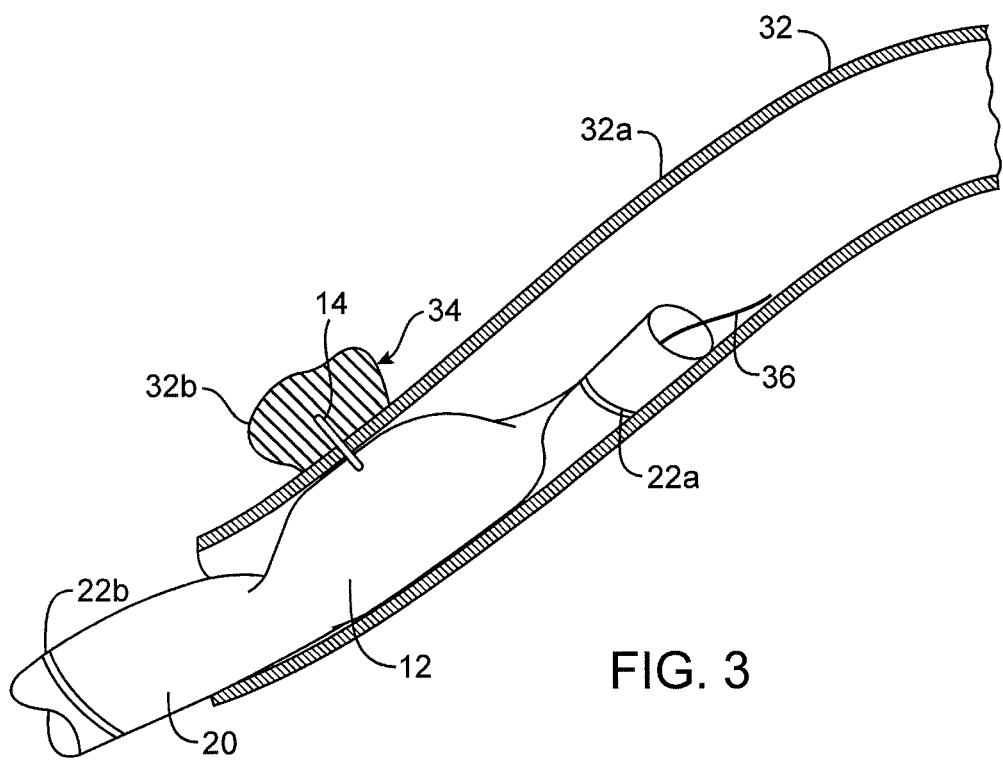
FIG. 3 is a schematic, perspective view of the microfabricated surgical device of the present invention inserted into a patient's vasculature.

The catheter 20, in use, is inserted through an artery or vein and moved within a patient's vasculature, for instance, an artery 32, until a specific, targeted region 34 is reaches (see FIG. 3). As is well known in catheter-based interventional procedures, the catheter 20 may follow a guide wire 36 that has previously been inserted into the patient. Optionally, the catheter 20 may also follow the path of a previously-inserted guide catheter (not shown) that encompasses the guide wire.

During maneuvering of the catheter 20, well-known methods of fluoroscopy or magnetic resonance imaging (MRI) can be used to image the catheter and assist in positioning the actuator 12 and the microneedle 14 at the target region. As the catheter is guided inside the patient's body, the microneedle remains unfurled or held inside the actuator body so that no trauma is caused to the vascular walls.

After being positioned at the target region 34, movement of the catheter is terminated and the activating fluid is supplied to the open area 26 of the actuator, causing the expandable section 24 to rapidly unfurl, moving the microneedle 14 in a substantially perpendicular direction, relative to the longitudinal central axis 12b of the actuator body 12a, to puncture a vascular wall 32a. It may take only between approximately 100 milliseconds and two seconds for the microneedle to move from its furled state to its unfurled state.

The ends of the actuator at the retaining rings 22a and 22b remain rigidly fixed to the catheter 20. Thus, they do not deform during actuation. Since the actuator begins as a furled structure, its so-called pregnant shape exists as an unstable buckling mode. This instability, upon actuation, produces a large-scale motion of the microneedle approximately perpendicular to the central axis of the actuator body, causing a rapid puncture of the vascular wall without a large momentum transfer. As a result, a microscale opening is produced with very minimal damage to the surrounding tissue. Also, since the momentum transfer is relatively small, only a negligible bias force is required to hold the catheter and actuator in place during actuation and puncture.

The microneedle, in fact, travels so quickly and with such force that it can enter perivascular tissue 32b as well as vascular tissue. Additionally, since the actuator is "parked" or stopped prior to actuation, more precise placement and control over penetration of the vascular wall are obtained.

After actuation of the microneedle and delivery of the pharmaceutical to the target region via the microneedle, the activating fluid is exhausted from the open area 26 of the actuator, causing the expandable section 24 to return to its original, furled state. This also causes the microneedle to be withdrawn from the vascular wall. The microneedle, being withdrawn, is once again sheathed by the actuator.

By way of example, the microneedle may have an overall length of between about 200 and 3,000 microns (μm). The interior cross-sectional dimension of the shaft 14b and supply tube 14d may be on the order of 20 to 250 μm, while the tube's and shaft's exterior cross-sectional dimension may be between about 100 and 500 μm. The overall length of the actuator body may be between about 5 and 50 millimeters (mm), while the exterior and interior cross-sectional dimensions of the actuator body can be between about 0.4 and 4 mm, and 0.5 and 5 mm, respectively. The gap or slit through which the central section of the actuator unfurls may have a length of about 4-40 mm, and a cross-sectional dimension of about 50-500 μm. The diameter of the delivery tube for the activating fluid may be about 100 μm to 1000 μm. The catheter size may be between 1.5 and 15 French (Fr).

Figure 4:
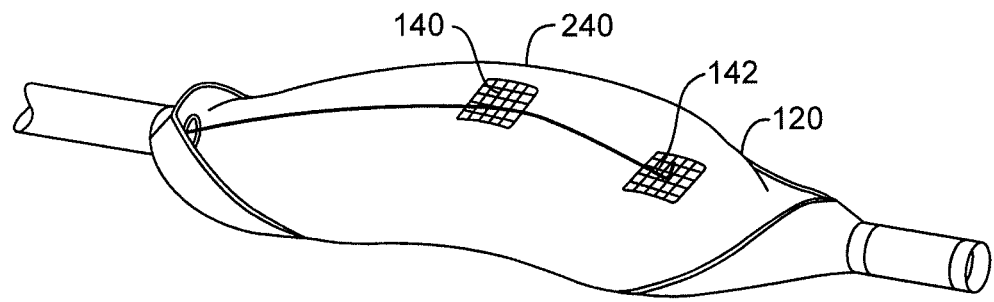
FIG. 4 is a schematic, perspective view of another embodiment of the device of the present invention.

Methods of the present invention may also utilize a multiple-buckling actuator with a single supply tube for the activating fluid. The multiple-buckling actuator includes multiple needles that can be inserted into or through a vessel wall for providing injection at different locations or times. For instance, as shown in FIG. 4, the actuator 120 includes microneedles 140 and 142 located at different points along a length or longitudinal dimension of the central, expandable section 240. The operating pressure of the activating fluid is selected so that the microneedles move at the same time. Alternatively, the pressure of the activating fluid may be selected so that the microneedle 140 moves before the microneedle 142.

Specifically, the microneedle 140 is located at a portion of the expandable section 240 (lower activation pressure) that, for the same activating fluid pressure, will buckle outwardly before that portion of the expandable section (higher activation pressure) where the microneedle 142 is located. Thus, for example, if the operating pressure of the activating fluid within the open area of the expandable section 240 is two pounds per square inch (psi), the microneedle 140 will move before the microneedle 142. It is only when the operating pressure is increased to four psi, for instance, that the microneedle 142 will move. Thus, this mode of operation provides staged buckling with the microneedle 140 moving at time $t_1$, and pressure $p_1$, and the microneedle 142 moving at time $t_2$ and $p_2$, with $t_1$, and $p_1$, being less than $t_2$ and $p_2$, respectively.

This sort of staged buckling can also be provided with different pneumatic or hydraulic connections at different parts of the central section 240 in which each part includes an individual microneedle.

Figure 5:
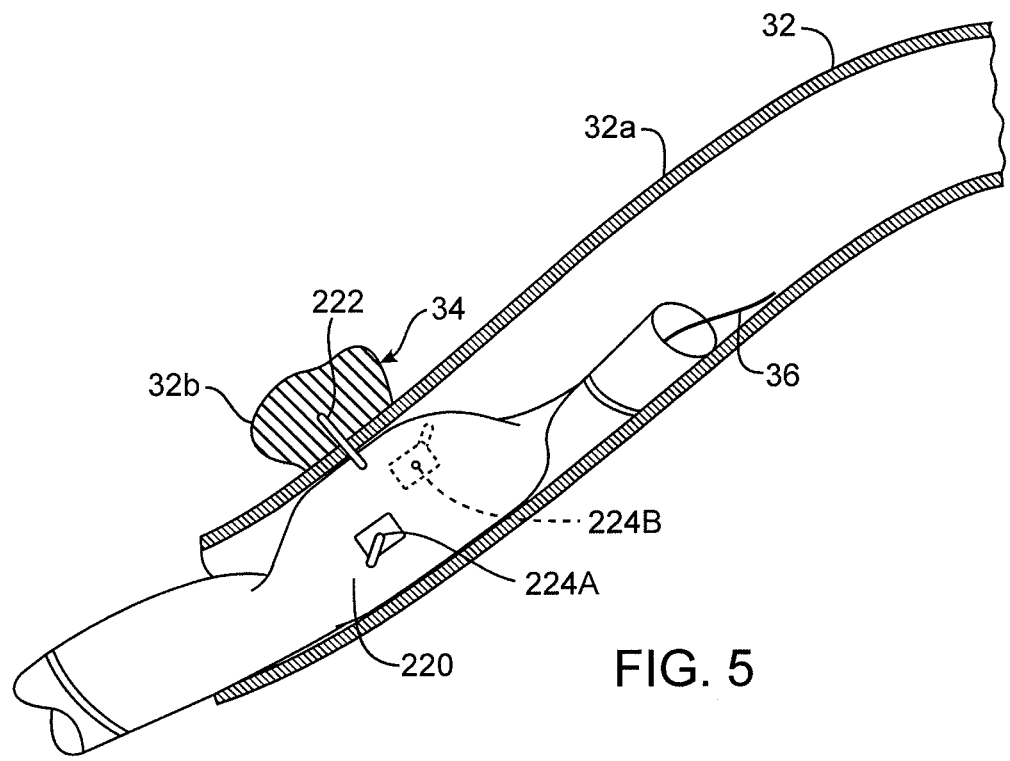
FIG. 5 is a schematic, perspective view of still another embodiment of the present invention, as inserted into a patient's vasculature.

Also, as shown in FIG. 5, an actuator 220 could be constructed such that its needles 222 and 224A move in different directions. As shown, upon actuation, the needles move at angle of approximately 90° to each other to puncture different parts of a vessel wall. A needle 224B (as shown in phantom) could alternatively be arranged to move at angle of about 180° to the needle 224A.

Referring now to FIGS. 6A/6B through FIGS. 8A/8B, use of the catheter 10 of FIGS. 1-3 for delivering a pharmaceutical agent according to the methods of the present invention will be described. The catheter 10 may be positioned so that the actuator 12 is positioned at a target site for injection within a blood vessel, as shown in FIGS. 6A/6B. The actuator penetrates the needle 14 through the wall W so that it extends past the external elastic lamina (EEL) into the perivascular space surrounding the EEL. Once in the perivascular space, the pharmaceutical agent may be injected, typically in a volume from 10 µl to 5000 µl, preferably from 100 µl to 1000 µl, and more preferably 250 µl to 500 µl, so that a plume P appears. Initially, the plume occupies a space immediately surrounding an aperture in the needle 14 and extending neither circumferentially nor longitudinally relative toward the external wall W of the blood vessel. After a short time, typically in the range from 1 to 10 minutes, the plume extends circumferentially around the external wall W of the blood vessel and over a short distance longitudinally, as shown in FIGS. 7A and 7B, respectively. After a still further time, typically in the range from 5 minutes to 24 hours, the plume will extend substantially completely circumferentially, as illustrated in FIG. 8A, and will begin to extend longitudinally over extended lengths, typically being at least about 2 cm, more usually being about 5 cm, and often being 10 cm or longer, as illustrated in FIG. 8B.

Figure 1D:
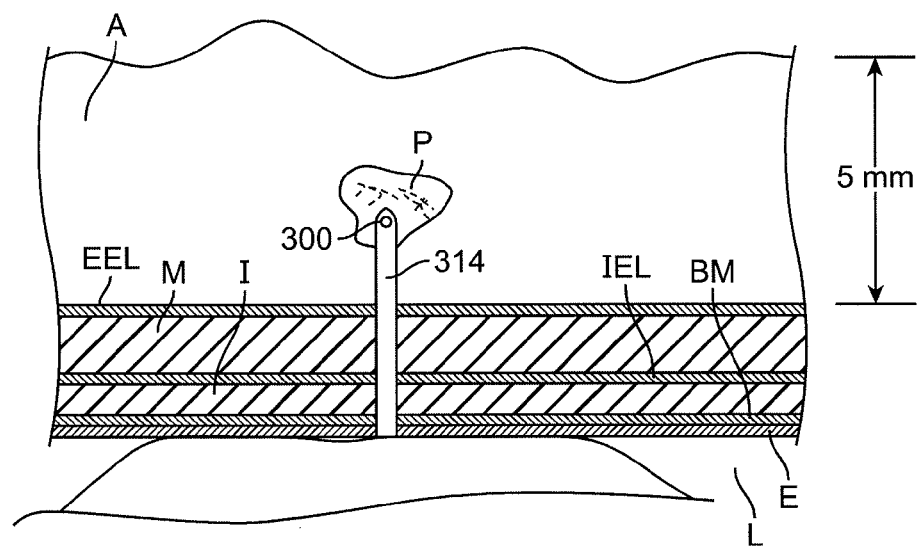
FIG. 1D is a schematic illustration of a microneedle having an aperture positioned at a preferred distance beyond the external elastic lamina (EEL) in accordance with the principles of the present invention.
Figure 1E:
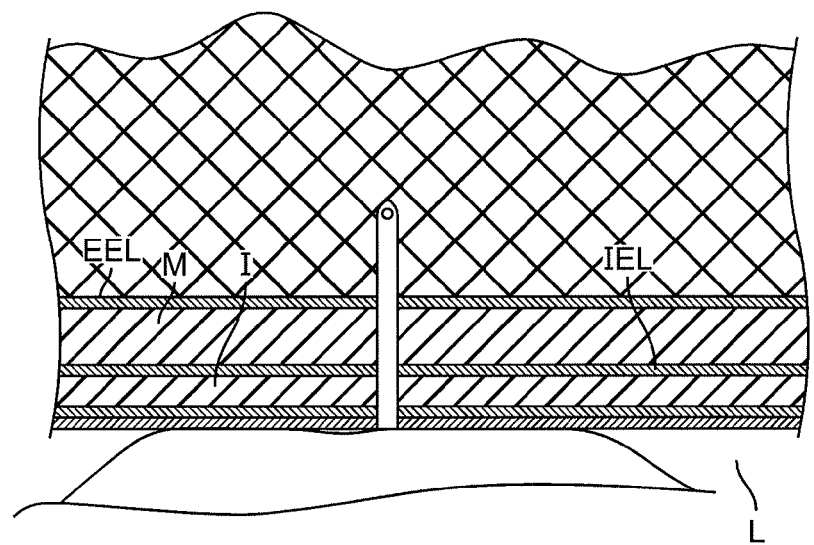
FIG. 1E illustrates the volumetric drug distribution achieved by the microneedle positioning of FIG. 1D.

Referring now to FIGS. 1D and 1E, a preferred protocol for positioning the aperture 300 of a microneedle 314 for volumetric delivery of a pharmaceutical agent in accordance with the principles of the present invention will be described. The aperture 300 is positioned from the lumen L of a blood vessel using any of the microneedle catheter systems described above. In particular, aperture 300 of the microneedle 314 is positioned beyond the external elastic lamina EEL by a distance of 5 mm or less, preferably 3 mm or less, and usually 0.5 mm or less, as described previously. To position the aperture within the requisite distance beyond the EEL, the needle must pass through the other layers of the blood vessel, as described above, in connection with FIG. 1A. Usually, these underlying layers will have a total thickness in the range from 0.1 mm to 5 mm, requiring that the needle extend from the blood vessel by a distance which is greater than the thickness of the wall. Once in position, the aperture 300 releases the pharmaceutical agent which then begins to form a plume P, as illustrated in FIG. 1D. By positioning beyond the blood vessel wall, but less than the 5 mm limit, it has been found that extensive volumetric distribution of the pharmaceutical agent can be achieved, as shown in FIG. 1E.

Because of variability in blood vessel wall thickness and obstructions which may limit the penetration depth of the needle being deployed, it will often be desirable to confirm that the pharmaceutical agent delivery aperture of the injection needle is present in the 5 mm annular envelope surrounding the delivery blood vessel prior to injection. Such confirmation can be achieved in a variety of ways.

Figure 3A:
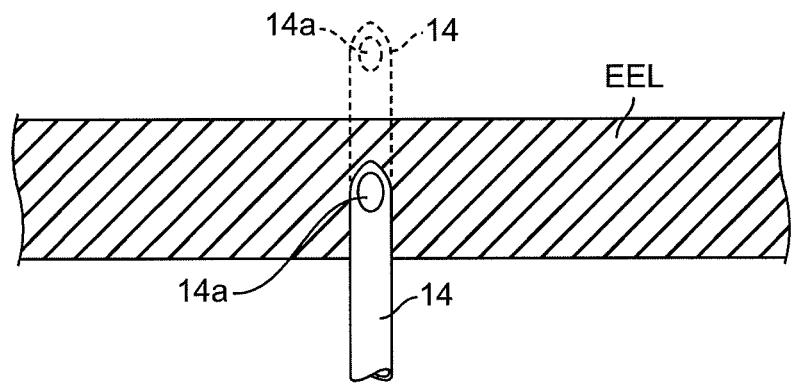
FIGS. 3A-3C illustrate the injection of a radio contrast media to help determine whether the pharmaceutical agent delivery aperture of an injection needle is properly placed within the preferred adventitial space surrounding a blood vessel.
Figure 3B:
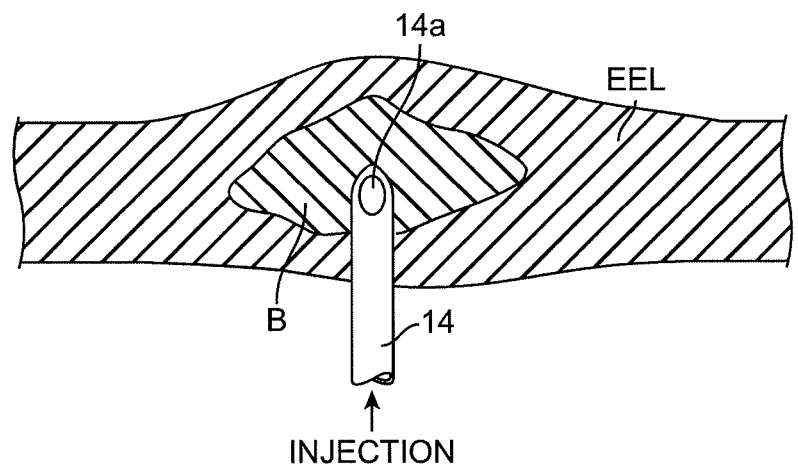
Figure 3C:
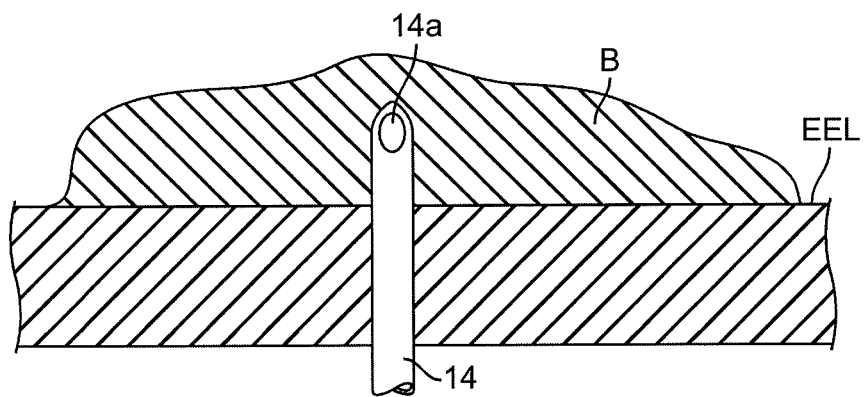
Figure 3D:
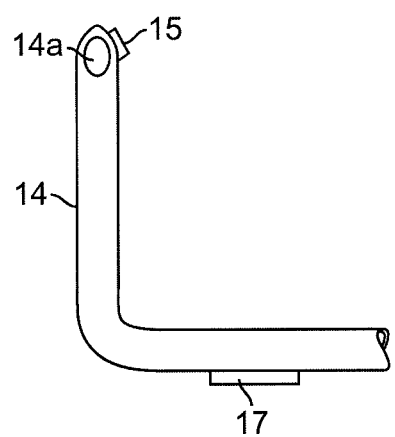
FIG. 3D illustrates the optional placement of sensors on a drug injection needle, which sensors can detect whether the needle has been advanced into the preferred adventitial space surrounding a blood vessel.

Referring to FIGS. 3A through 3C, the needle 14 of FIG. 3 can be positioned through the vascular wall so that it lies beyond the external elastic lamina (EEL), as shown in broken line in FIG. 3A. So long as the aperture 14a lies beyond the periphery of the EEL, and preferably a 5 mm annulus surrounding the vessel, successful delivery of the pharmaceutical agent can usually be achieved. To confirm that the aperture 14a lies within this target annual region, a bolus of contrast media can be injected prior to delivery of the pharmaceutical agent. If the aperture 14a has not penetrated through the EEL, as shown in FIG. 3B, then the bolus of contrast media will remain constrained within the wall of the vessel forming a well defined, generally tapered or ovoid mass B, as shown in FIG. 3B. In contrast, if the aperture 14a is positioned beyond the EEL, and within the desired annular region, the bolus B will spread longitudinally along the blood vessel wall in a very short period of time, indicating that the drug may be affectively delivered, as shown in FIG. 3C.

Other methods for confirming that the aperture 14a is properly positioned rely on presence of a sensor(s) 15 and/or located on the needle 14 usually near the aperture. Sensor 15 may be a solid state pressure sensor. If the pressure builds up during injection (either of an inactive agent or the pharmaceutical agent, it is likely that the aperture 14a still lies within the blood vessel wall. If the pressure is lower, the physician can assume that the needle has reached the adventitia. Sensor 15 may also be a temperature, such as a small thermistor or thermocouple, located at the tip of the needle adjacent over then the aperture 14a. The temperature within the blood vessel wall will be different than that outside of the EEL, making position function of temperature. The sensor may be a pH detector, where the tissue within the blood vessel wall and beyond the EEL have detectable differences in pH. Similarly, electrical impedance measurements characteristic of the tissues may be made with an impedance sensor 15. A deflection sensor 17, such as a flexible straining gauge, may be provided on a portion of the needle 14 which will deflect in response to insertion force. Insertion force through the blood vessel wall will be higher than that necessary to penetrate the tissue beyond the EEL. Thus, entry into the tissue beyond the EEL can be confirmed when the insertion force measured by the sensor 17 falls.

As just described, of course, the extent of migration of the pharmaceutical agent is not limited to the immediate region of the blood vessel through which the agent is been injected into the perivascular space. Instead, depending on the amounts injected and other conditions, the pharmaceutical agent may extend further into and through the myocardium other connective tissues so that it surrounds the extravascular spaces around other blood vessels, including both arteries and veins. As also described above, such broad myocardial, epicardial, or pericardial delivery can be particularly useful for treating non-localized cardiac conditions, such as conditions associated with congestive heart failure conditions associated with vulnerable or unstable plaque and conditions associated with cardiac arrhythmias. Delivery and diffusion of a pharmaceutical agent into a peripheral extravascular space can be particularly useful for treating diffuse vascular diseases.

The methods and kits described above may be used to deliver a wide variety of pharmaceutical agents intended for both local and non-local treatment of the heart and vasculature. Exemplary pharmaceutical agents include antineoplastic agents, antiproliferative agents, cytostatic agents, immunosuppressive agents, anti-inflammatory agents, macrolide antibiotics, antibiotics, antifungals, antivirals, antibodies, lipid lowering treatments, calcium channel blockers, ACE inhibitors, gene therapy agents, anti-sense drugs, double stranded short interfering RNA molecules, metalloproteinase inhibitors, growth factor inhibitors, cell cycle inhibitors, angiogenesis drugs, anti-angiogenesis drugs, and/or radiopaque contrast media for visualization of the injection under guided X-ray fluoroscopy. Each of these therapeutic agents has shown promise in the treatment of cardiovascular disease, restenosis, congestive heart failure, and/or vulnerable plaque lesions. Particular agents are set forth in Table I.

The following Experiments are offered by way of illustration, not by way of limitation.

EXPERIMENTAL

Studies were performed to show visual and quantitative evidence of depostion of agents in the adventitia and distribution of the deposited agents from that site.

Distribution of fluorescent-labeled drug: Oregon Green® 488 paclitaxel (OGP) was injected into balloon-injured or normal porcine coronary arteries (15 arteries, 6 pigs) using a microneedle injection catheter having a needle with a diameter of 150 µm. Injections were made to depths in the range from 0.8 mm to 1.2 mm One artery was treated intraluminally with 5 mL OGP to determine background vascular uptake. Animals were sacrificed 0.5-23 hr post-procedure following IACUC-approved protocol. After sacrifice, the LAD, RCA and LCx were removed, cut into 4-5 mm sections, which were frozen and cryosectioned. The slides were counter-stained with 0.1% Evan's Blue in PBS (5 min 37 C) to quench autofluorescence, observed with a UV microscope, and scored 0-4+. Representative sections were photographed.

Acutely harvested tissue (<2 hr post-procedure) showed 4+ staining of the adventitia when OGP was delivered with the microneedle catheter through the vessel wall. With increasing time after delivery, drug penetrated into the media and

TABLE I

1. Antiproliferative agents, immunosuppressive agents, cytostatic, and anti-inflammatory agents, including but not limited to sulindac, tranilast, ABT-578, AVI-4126, sirolimus, tacrolimus, everolimus, cortisone, dexamethosone, cyclosporine, cytochalisin D, valsartin, methyl prednisolone, thioglitazones, acetyl salicylic acid, sarpognelate, and nitric oxide releasing agents, which interfere with the pathological proliverative response after coronary antioplasty to prevent intimal hyperplasia, smooth muscle cell activation and migration, and neointimal thickening.
2. Antineoplastic agents, including but not limited to paclitaxel, actinomycin D, and latrunculin A, which interfere with the pathological proliferative response after coronary angioplasty to prevent intimal hyperplasia, smooth muscle activation and migration and neointimal thickening.
3. Macrolide antibiotics, including but not limited to sirolimus, tacrolimus, everolimus, azinthromycin, clarithromycin, and erythromycin, which inhibit or kill microorganiss that may contribute to the inflammatory process that triggers or exacerbates restenosis and vulnerable plaque. In addition many macrolide antibiotics, including but not limited to sirolimus and tacrolimus, have immunosuppressive effects that can prevent intimal hyperplasia, neointimal proliferation, and plaque rupture. Other antibiotics, including but not limited to sirolumus, tacrolimus, everolimus, azithromycin, clarithromycin, doxycycline, and erothromycin, inhibit or kill microorganisms that may contribute to the inflammatory process that triggers or exacerbates restenosis and vulnerable plaque.
4. Antivirals, including but not limited to acyclovir, ganciclovir, fancyclovir and valacyclovir, inhibit or kill viruses that may contribute to the inflammatory process that triggers or exacerbates restenosis and vulnerable plaque.
5. Antibodies which inhibit or kill microorganisms that may contribute to the inflammatory process that triggers or exacerbates restenosis and vulnerable plaque or to inhibit specific growth factors or cell regulators.
6. Lipid-lowering treatments, including but not limited to statins, such as trichostatin A, which modify plaques, reducing inflammation and stabilizing vulnerable plaques.
7. Gene therapy agents which achieve overexpression of genes that may ameliorate the process of vascular occlusive disease or the blockade of the expression of the genes that are critical to the pathogenesis of vascular occlusive disease.
8. Anti-sense agents, including but not limited to AVI-4126, achieve blockade of genes and mRNA, including but not limited to c-myc, c-myb, PCNA, cdc2, cdk2, or cdk9s, through the use of short chains of nucleic acids known as antisense oligodeoxynucleotides.
9. Metalloproteinase inhibitors, including but not limited to batimastat, inhibit constrictive vessel remodeling.
10. Cell cycle inhibitors and modulators and growth factor inhibitors and modulators, including but not limited to cytokine receptor inhibitors, such as interleukin 10 or propagermanium, and modulators of VEGF, IGF, and tubulin, inhibit or modulate entry of vascular smooth muscle cells into the cell cycle, cell migration, expression chemoattractants and adhesion molecules, extracellular matrix formation, and other factors that trigger neointimal hyperplasia.
11. Angiogenesis genes or agents which increase microvasculature of the pericardium, vaso vasorum, and adventitia to increase blood flow.
12. Anti-angiogenesis genes or agents inhibit factors that are associated with microvascularization of atherosclerotic plaque and which directly or indirectly also induce smooth muscle cell proliferation.
13. Antithrombotics including but not limited to IIb/IIIa inhibitors, Abciximab, heparin, clopidigrel, and warfarin.

extended longitudinally 13-24 mm (mean, 15 mm) from the injection site. At 23 hr, staining was observed throughout the circumference of the artery, with longitudinal extension of 23-32 mm (mean, 27.5 mm). OGP delivered into the lumen without needle deployment resulted in staining on the luminal surface only.

Distribution of silver nitrate: Two injections of 0.5 mL 5% Silver Nitrate were made into each iliac artery of a rabbit. The animal was sacrificed according to approved protocol following the last injection. The arteries were removed and placed in 10% formalin without perfusion. 2 mm segments were embedded in paraffin, sectioned, and hematoxylin-eosin stained.

Staining showed delivery outside the external elastic lamina of the vessels and diffusion around the circumference.

Distribution of a lipophilic compound (tacrolimus): Eight swine underwent angiography. Twenty-two coronary arteries (2.25-2.75 mm) received 125 micrograms tacrolimus in two 500 micrograms injections approximately 1 cm apart. The two remaining arteries served as untreated controls. An untreated heart was used as a negative control. At 48 hours arteries were dissected from the musculature and perivascular fat, cut into 5 mm sections and analyzed by Liquid Chromatography/Mass Spectrometry against tacrolimus calibration standards containing homogenized untreated porcine heart tissue.

Figure 9:
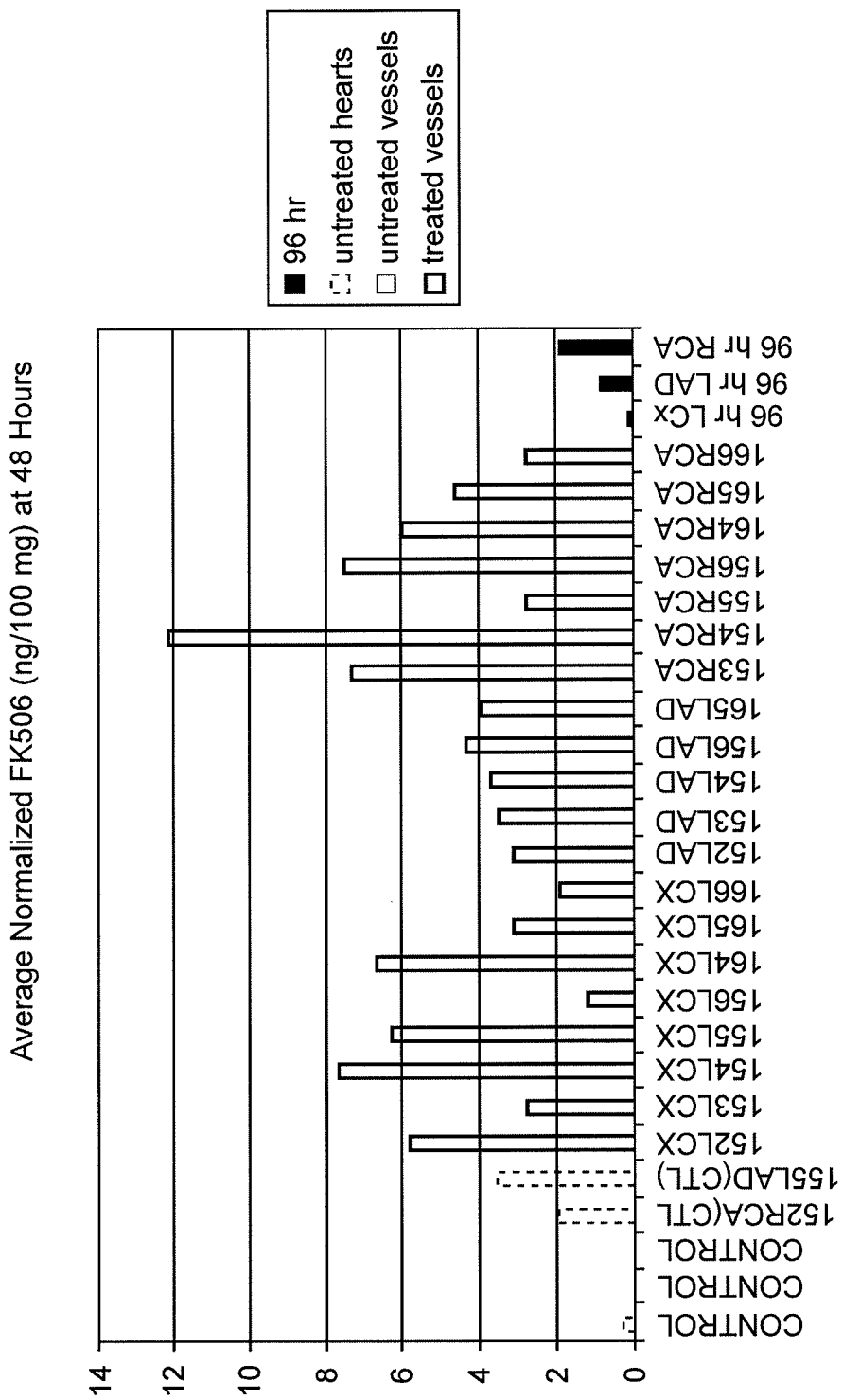
FIGS. 9 and 10 illustrate data described in the Experimental section herein.
Figure 10:
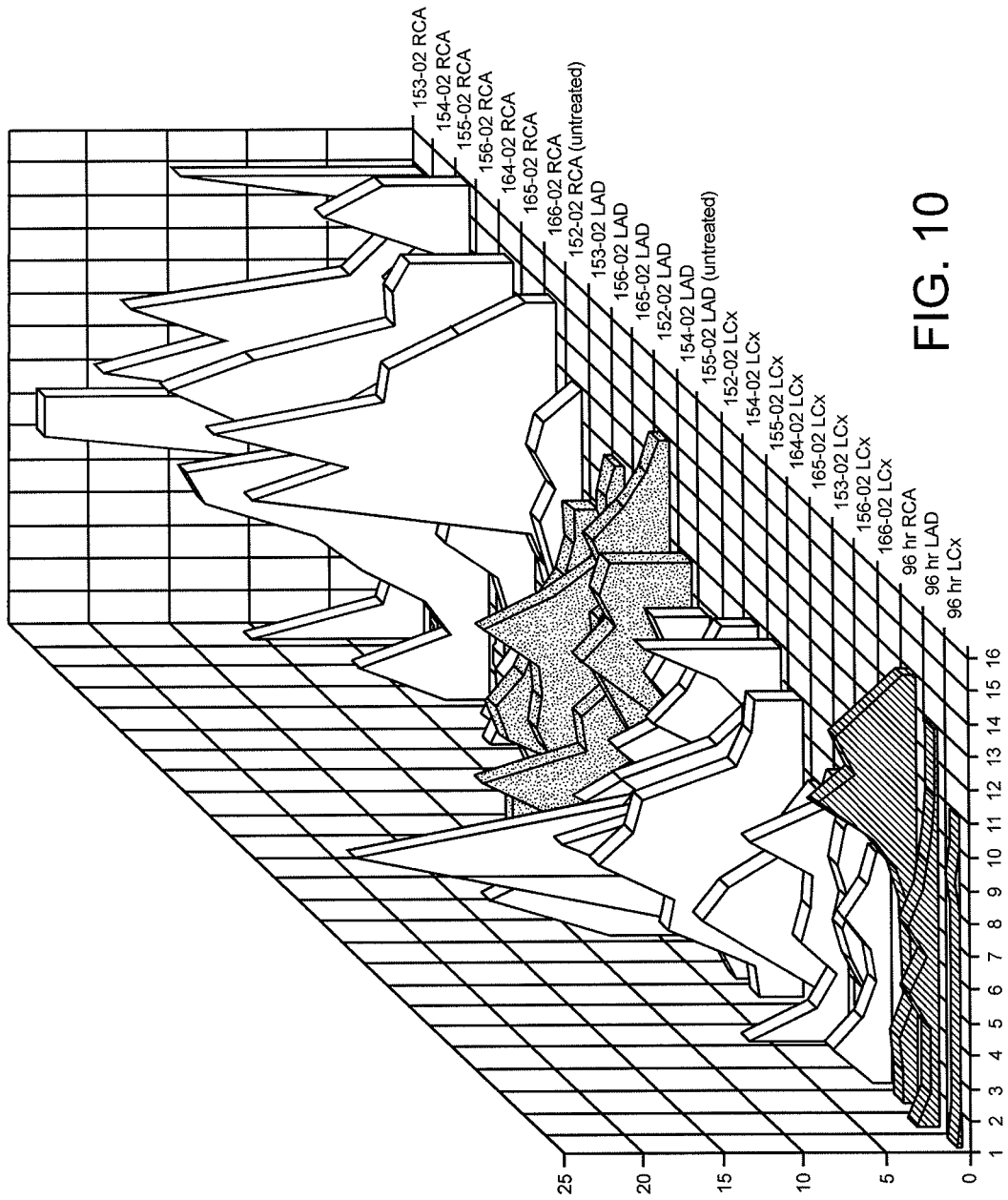

In 8/8 subjects, periadventitial delivery of tacrolimus resulted in distribution to the entire coronary tree with higher concentrations at injection sites. Drug was detected in 285/293 segments, including side branches and uninjected arteries. The mean levels of tacrolimus were 5.5 ng/100 mg tissue (SD=2.5, N=15) in the confirmed injected arteries, 2.7 ng/100 mg tissue (SD=1.1, N=2) in uninjected arteries of treated hearts, and 0.08 ng/100 mg tissue (SD=0.14, N=3) in uninjected arteries of the untreated heart. Mean concentration within 1 cm of known injection sites was 6.4 ng/100 mg tissue (SD=3.7, N=13) versus 2.6 ng/100 mg tissue (SD=1.5, N=13) in the remaining segments (p<0.001). Data are provided in FIGS. 9 and 10.

The microsyringe delivered agent to the adventitia, demonstrated by circumferential and longitudinal arterial distribution of fluorescent-labeled paclitaxel and silver nitrate. The paclitaxel studies showed that the distribution increased over time. Quantitative measurement of tacrolimus showed distribution of drug the full length of the artery, which was detectable 48 hours after injection.

A number of embodiments of the invention have been described. Nevertheless, it will be understood that various modifications may be made without departing from the spirit and scope of the invention as claimed hereinafter.

What is claimed is:

1. An improved method for injecting a pharmaceutical agent into the adventitial tissue of a living host using a needle positioned from a lumen of a blood vessel, wherein the improvement comprises penetrating the needle radially outwardly from the blood vessel lumen through a blood vessel wall and an external elastic lamina (EEL) and into adventitial tissue surrounding the lumen, injecting a fluid through the needle, monitoring backpressure to confirm that a delivery aperture of the needle has penetrated through the blood vessel wall and beyond the external elastic lamina of the blood vessel and into the adventitial tissue, and observing the backpressure lower as the delivery aperture of the needle passes through the EEL and into the adventitial tissue, wherein such a lowering of the backpressure confirms entry of the delivery aperture of the needle into the adventitial tissue.

2. A method as in claim 1, wherein the injected fluid comprises a non-active agent and the pharmaceutical agent is delivered only after confirming that the delivery aperture of the needle is in the adventitial tissue.

3. A method as in claim 2, wherein the non-active agent comprises saline.

4. A method as in claim 1, wherein the fluid is the pharmaceutical agent.

5. A method as in claim 4, wherein pharmaceutical agent comprises a small molecule drug, a protein, or a gene.

6. A method as in claim 5, wherein the agent has a maximum dimension of 200 nm or below.

7. A method as in claim 1, wherein the delivery aperture of the needle is positioned at a distance less than 5 mm beyond the EEL.

8. A method as in claim 1, wherein the blood vessel is a coronary blood vessel.

9. A method as in claim 8, wherein the coronary blood vessel is an artery.

10. A method as in claim 9, wherein the artery is at risk of hyperplasia.

11. A method as in claim 9, wherein the artery has regions of vulnerable plaque.

12. A method as in claim 1, wherein the living host is suffering from congestive heart failure or a cardiac arrhythmia.

13. A method as in claim 1, wherein the blood vessel is a cerebral blood vessel and the adventitial tissue is in the brain of the host.

14. A method as in claim 1, wherein the blood vessel is a hepatic blood vessel and the adventitial tissue is in the liver of the host.

15. A method as in claim 1, wherein the pharmaceutical agent is being delivered to treat a neoplastic disease in the adventitial tissue.

16. An improved method for injecting a pharmaceutical agent into the adventitial tissue of a living host using a needle positioned from a lumen of a blood vessel, wherein the method comprises positioning the needle by deploying the needle radially outwardly from the blood vessel lumen into a blood vessel wall, confirming that placement of a delivery aperture of the needle is beyond the external elastic lamina (EEL) of the blood vessel wall and is in the adventitial tissue by injecting a fluid through the needle following needle positioning and monitoring backpressure during injection, wherein placement of the delivery aperture is confirmed to be in adventitial tissue when the backpressure during injection is lower than the backpressure that would exist during injection when the delivery aperture placement is in the blood vessel wall.

17. A method as in claim 16, wherein the injected fluid comprises a non-active agent and the pharmaceutical agent is delivered only after confirming that the delivery aperture of the needle is in the adventitial tissue.

18. A method as in claim 17, wherein the non-active agent comprises saline.

19. A method as in claim 16, wherein the fluid is the pharmaceutical agent.

20. A method as in claim 19, wherein pharmaceutical agent comprises a small molecule drug, a protein, or a gene.

21. A method as in claim 20, wherein the agent has a maximum dimension of 200 nm or below.

22. A method as in claim 16, wherein the delivery aperture of the needle is positioned at a distance less than 5 mm beyond the EEL.

* * * * *